United States Patent [19]

Rauleder et al.

[11] Patent Number: 5,468,706

[45] Date of Patent: Nov. 21, 1995

[54] STORAGE-STABLE SOLUTION OF A MIXTURE OF CARBONATED MAGNESIUM METHOXIDE, CARBONATED MAGNESIUM ETHOXIDE AND THEIR CARBONATED MIXED ALKOXIDE IN A COMBINATION OF METHANOL AND ETHANOL AND USES THEREOF

[75] Inventors: Hartwig Rauleder; Burkhard Standke; Hans-Joachim Kötzsch; Reinhold Schork, all of Rheinfelden, Germany

[73] Assignee: Huels Aktiengesellschaft, Marl, Germany

[21] Appl. No.: 167,354

[22] Filed: Dec. 15, 1993

[30] Foreign Application Priority Data

Jan. 7, 1993 [DE] Germany ............... 43 00 185.8

[51] Int. Cl.$^6$ .................. C07F 3/02; D21H 17/12; D21H 25/02; B01J 31/12

[52] U.S. Cl. .................. 502/151; 502/152; 502/156; 502/171; 502/172; 427/439; 106/287.23; 252/380; 252/397; 252/399; 252/400.61

[58] Field of Search .................. 427/421, 430.1, 427/439; 252/380, 397, 399, 400.1, 400.61; 502/151, 152, 156, 171, 172; 106/287.23

[56] References Cited

U.S. PATENT DOCUMENTS

| | | | |
|---|---|---|---|
| 3,939,091 | 2/1976 | Kelly, Jr. ................ | 252/189 |
| 3,969,549 | 7/1976 | Williams et al. ............ | 427/248 |
| 4,318,963 | 3/1982 | Smith ..................... | 428/537 |
| 4,540,679 | 9/1985 | Arzoumanidis et al. ........ | 502/111 |
| 4,860,685 | 8/1989 | Smith ..................... | 427/421 |
| 4,866,022 | 9/1989 | Arzoumanidis et al. ........ | 502/120 |
| 4,988,656 | 1/1991 | Arzoumanidis et al. ........ | 502/127 |
| 5,013,702 | 5/1991 | Arzoumanidis et al. ........ | 502/120 |
| 5,104,997 | 4/1992 | Kamienski et al. ........... | 427/430.1 |
| 5,208,072 | 5/1993 | Kamienski et al. ........... | 427/439 |
| 5,210,334 | 5/1993 | Standke et al. ............. | 568/851 |
| 5,227,542 | 7/1993 | Horns et al. ............... | 568/851 |
| 5,322,558 | 6/1994 | Wittekind et al. ........... | 106/287.23 |

FOREIGN PATENT DOCUMENTS

| | | |
|---|---|---|
| 0159150 | 10/1985 | European Pat. Off. . |
| 0236082 | 9/1987 | European Pat. Off. . |
| 0285227 | 10/1988 | European Pat. Off. . |
| 0436801 | 7/1991 | European Pat. Off. . |
| 0491128 | 6/1992 | European Pat. Off. . |

OTHER PUBLICATIONS

Reagents for Organic Synthesis, pp. 631–633, L. F. Fieser, et al., "Magnesium Methyl Carbonate (MMC), CH3OMgOCO2CH3+XCO2" (no date).

*Primary Examiner*—Asok Pal
*Assistant Examiner*—Walter D. Griffin
*Attorney, Agent, or Firm*—Oblon, Spivak, McClelland, Maier & Neustadt

[57] ABSTRACT

The present invention relates to a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$, in which $0<x, y<2$ and $x+y=2$, in a combination of methanol and ethanol, and processes for the preparation thereof, the magnesium content of the solution being from 0.1 to 11% by weight, based on the total weight of the solution, and the $CO_2$ content n being from 1.0 to 2.2. The present solutions are used, inter alia, for the preservation of paper and for the preparation of a catalyst for the polymerization of olefins.

5 Claims, No Drawings

STORAGE-STABLE SOLUTION OF A MIXTURE OF CARBONATED MAGNESIUM METHOXIDE, CARBONATED MAGNESIUM ETHOXIDE AND THEIR CARBONATED MIXED ALKOXIDE IN A COMBINATION OF METHANOL AND ETHANOL AND USES THEREOF

BACKGROUND OF THE INVENTION

1 Field of the Invention

The present invention relates to a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, and processes for their preparation. The present invention also relates to the use of the storage-stable solution of a mixture of carbonated magnesium methoxide, carbonated magnesium ethoxide and their carbonated mixed alkoxide in a combination of methanol and ethanol for the preservation of paper and for the preparation of a catalyst for the polymerization of olefins.

2 Discussion of the Background

Magnesium alcoholates are, as a rule, not very soluble in the corresponding alcohols. In some cases, magnesium alcoholates are virtually insoluble in the corresponding alcohols. An exception is magnesium methoxide, which has a solubility of up to about 12% by weight in methanol.

A technically simple method for increasing the solubility of magnesium alcoholates is carbonation. Gaseous, liquid or solid $CO_2$ is introduced into a suspension of the magnesium alcoholate in the corresponding alcohol. A soluble $CO_2$ adduct forms. In the case of magnesium ethoxide, the $CO_2$ adduct is soluble up to a concentration of more than 30% by weight in ethanol, whereas pure magnesium ethoxide is virtually insoluble in ethanol.

Alcohol-soluble carbonated magnesium alkoxides are widely used. Thus, for example, magnesium alkoxides brought into solution by carbonation can be used in the long-term preservation of paper. This utility of soluble carbonated magnesium alkoxides is particularly useful in the manufacture of books. Soluble carbonated magnesium alkoxides can be substituted for zinc alkyls, which are also used for this purpose, according to U.S. Pat. No. 3,969,549, EP-A 0,285,227, U.S. Pat. No. 4,318,963 and U.S. Pat. No. 3,939,091, but which present problems during use.

According to European Pat. No. 0,159,150 and European Pat. No. 0,236,082, a further field of use is the preparation of catalysts for the polymerization of olefins. For example, spherical magnesium methoxide and magnesium ethoxide are useful for this purpose. Spherical magnesium methoxide and magnesium ethoxide can be prepared, for example, by spray drying or precipitation of carbonated magnesium methoxide solutions or magnesium ethoxide solutions, and, if required, subsequent decarbonation.

It is known in principle that solutions of carbonated magnesium alcoholates can be prepared according to the two reaction schemes below. On the one hand, metallic magnesium can be reacted with an alcohol ROH and $CO_2$ (equation (1)). On the other hand, a magnesium alkoxide can be reacted with $CO_2$ (equation (2)):

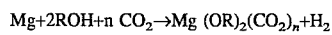

$$Mg + 2ROH + n\ CO_2 \rightarrow Mg(OR)_2(CO_2)_n + H_2 \qquad (1)$$

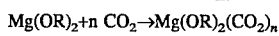

$$Mg(OR)_2 + n\ CO_2 \rightarrow Mg(OR)_2(CO_2)_n \qquad (2)$$

Here, R denotes an alkyl group, preferably a branched or linear $C_1$–$C_4$ alkyl group.

European Pat. 0,236,082 teaches the preparation of carbonated magnesium alkoxides by reacting magnesium alkoxides with $CO_2$ in a solvent. Preferred solvents are alcohols. For example, the preparation of carbonated magnesium ethoxide by reacting magnesium ethoxide with $CO_2$ in ethanol as a solvent is disclosed.

In "Reagents for Organic Synthesis" (vol. 1, page 631), Fieser et al describe the preparation of carbonated magnesium methoxide by two different routes. In one procedure, a suspension of magnesium methoxide in methanol is reacted with $CO_2$. In the other, magnesium turnings are reacted with methanol to give magnesium methoxide. After the methanol has been partially stripped off at 50° C. and under reduced pressure, dimethylformamide is added as a solvent, and $CO_2$ is passed into this solution. The remaining methanol is distilled off, and a slightly yellow solution of carbonated magnesium methoxide in dimethylformamide is obtained.

European Pat. 0,159,150 reports on the use of solutions of carbonated magnesium alcoholates in alcohols for the preparation of active catalyst carriers for olefin polymerization. The solutions used contain 10 to 80% by weight of magnesium alcoholate, and 0.1 to 4 mol of $CO_2$ per mol of magnesium. The solutions are prepared by reacting magnesium alcoholate, dispersed in alcohol, with gaseous $CO_2$.

However, the alcoholic solutions of carbonated magnesium alkoxides according to the references cited above are yellow to red in color. The discoloration may increase with increasing storage time. In addition, precipitation or gel formation can occur after only a few days on storage, even in tightly sealed vessels. The industrial use of such solutions is considerably limited. For example, colored solutions cannot be used for the long-term preservation of books. In addition, solutions in which there is a danger of uncontrolled precipitation cannot be used for the preparation of magnesium alkoxide-based catalysts.

SUMMARY OF THE INVENTION

Accordingly, one object of the present invention is to provide a novel storage-stable solution of magnesium alkoxide(s), which remains virtually colorless even over a relatively long period of time, and which exhibits neither precipitation nor gel formation.

As a result of establishing defined magnesium and $CO_2$ concentrations in a solution of a mixture of carbonated magnesium methoxide, carbonated magnesium ethoxide and their carbonated mixed alkoxide in a combination of methanol and ethanol, it has now been surprisingly found that coloration, precipitation and gel formation do not occur, even during storage over long periods of time.

DETAILED DESCRIPTION OF THE PREFERRED EMBODIMENTS

The present invention therefore relates to a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, wherein the magnesium content of the solution is from 0.1 to 11% by weight, based on the total weight of the solution, and the $CO_2$ content n is from 1.0 to 2.2., Preferably, the present storage-stable solution has a magnesium content of from 3 to 11% by weight, and more preferably, from 5 to 11% by weight, based on the total weight of the solution. Preferably, the present storage-stable solution has a $CO_2$ content n of from 1.1 to 2.2, and more preferably, from 1.2 to 2.2.

The present invention furthermore relates to a process for the preparation of a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, comprising:

reacting a reaction mixture selected from the group consisting of (i) magnesium ethoxide in methanol, (ii) magnesium ethoxide and magnesium methoxide in methanol, (iii) magnesium methoxide in ethanol, (iv) magnesium methoxide and magnesium ethoxide in ethanol and/or (v) a mixed alkoxide of the formula $Mg(CH_3O)_x (C_2H_5O)_y$, x and y each being greater than 0 and less than 2 and the sum of x and y being equal to 2, in methanol, ethanol or both methanol and ethanol with $CO_2$, and adjusting the magnesium content of the solution to a value of from 0.1 to 11% by weight, based on the total weight of the solution, and the $CO_2$ content to a value n from 1.0 to 2.2, preferably from 1.2 to 2.2. Preferably, reaction mixture (v) above is in ethanol or methanol.

The present invention further concerns a process for the preparation of a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, comprising:

reacting magnesium ethoxide, magnesium methoxide, a mixed alkoxide of the formula $Mg(CH_3O)_x (C_2H_5O)_y$, x and y each being greater than 0 and less than 2 and the sum of x and y being equal to 2, or a mixture thereof, in methanol, ethanol, or a combination of methanol and ethanol with $CO_2$, and adjusting the magnesium content to a value of from 0.1 to 11% by weight, based on the total weight of the solution, and the $CO_2$ content to a value n of from 1.0 to 2.2, preferably from 1.2 to 2.2. Preferably, reaction mixture (v) above is in ethanol or methanol.

The present invention also relates to a process for the preparation of a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, comprising:

reacting metallic magnesium with $CO_2$ and a solvent selected from the group consisting of methanol, ethanol, and a combination of methanol and ethanol, and adjusting the magnesium content of the solution to a value of from 0.1 to 11% by weight, based on the total weight of the solution, and the $CO_2$ content to a value n of from 1.0 to 2.2, preferably from 1.2 to 2.2.

The present solution can also be made directly, without the need for an adjusting step. Accordingly, the present invention also concerns processes for the preparation of a storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, comprising reacting:

(A) a reaction mixture selected from the group consisting of (i) magnesium ethoxide in methanol, (ii) magnesium ethoxide and magnesium methoxide in methanol, (iii) magnesium methoxide in ethanol, (iv) magnesium methoxide and magnesium ethoxide in ethanol and (v) a mixed alkoxide of the formula $Mg(CH_3O)_x (C_2H_5O)_y (CO_2)_n$, x and y each being greater than 0 and less than 2 and the sum of x and y being equal to 2, in methanol, ethanol or both methanol and ethanol, with an amount of $CO_2$ sufficient to provide a $CO_2$ content n of from 1.0 to 2.2, wherein the magnesium methoxide, magnesium ethoxide, mixed alkoxide of the formula $Mg(CH_3O)_x (C_2H_5O)_y (CO_2)_n$ or any mixture thereof is present in the reaction mixture in an amount sufficient to provide a magnesium content of from 0.1 to 11% by weight, based on the total weight of the solution;

(B) magnesium ethoxide, magnesium methoxide, a mixed alkoxide of the formula $Mg(CH_3O)_x (C_2H_5O)_y$, x and y each being greater than 0 and less than 2 and the sum of x and y being equal to 2, or a mixture thereof in a combination of methanol and ethanol with an amount of $CO_2$ sufficient to provide a $CO_2$ content n of from 1.0 to 2.2, wherein the magnesium methoxide, magnesium ethoxide, mixed alkoxide of the formula $Mg(CH_3O)_x (C_2H_5O)_y (CO_2)_n$ or mixture thereof is present in an amount sufficient to provide a magnesium content of from 0.1 to 11% by weight, based on the total weight of the solution; or (C) an amount of metallic magnesium with amounts of methanol and ethanol sufficient to produce a solution with a magnesium content of from 0.1 to 11% by weight, based on the total weight of the solution, and an amount of $CO_2$ sufficient to provide a $CO_2$ content n of from 1.0 to 2.2.

The present invention further relates to the use of the present storage-stable solution of a mixture of carbonated magnesium methoxide, carbonated magnesium ethoxide and their carbonated mixed alkoxide in combination of methanol and ethanol for the preservation of paper, and to the use of the present storage-stable solution of a mixture of carbonated magnesium methoxide, carbonated magnesium ethoxide and their carbonated mixed alkoxide in a combination of methanol and ethanol for the preparation of a catalyst for the polymerization of olefins.

In the preparation of the present solutions, either metallic magnesium (see equation (1) above) or one or more of magnesium ethoxide and/or magnesium methoxide and/or their mixed alkoxide (see equation (2) above) serves as the magnesium source.

The use of metallic magnesium is economically more advantageous. For example, magnesium ethoxide is usually obtained from magnesium metal by reaction with ethanol. Therefore, a reaction step is dispensed with when metallic magnesium is used. Furthermore, products of higher color quality can be produced in the reaction of metallic magnesium with $CO_2$ and a combination of methanol and ethanol.

Thus, in the reaction of metallic magnesium with $CO_2$ and a combination of methanol and ethanol, solutions according to the present invention are obtained which have slightly lower color numbers, measured according to the Gardner method of measurement, compared with the solutions prepared, for example, from reacting either magnesium ethoxide in methanol or magnesium methoxide in ethanol with $CO_2$.

In the reaction of metallic magnesium with $CO_2$ and a combination of methanol and ethanol, the surface of the magnesium is continuously exposed, due to the solubility of the carbonated magnesium methoxide, of the carbonated magnesium ethoxide and of their carbonated mixed alkoxide. Thus, no passivation of the metal surface occurs as a result of the formation of an insoluble boundary layer between metal and methanol and/or ethanol. In the context of the present application, "passivation" refers to reaction of the metal with an oxidizing agent, which may result in inactivation of the metal surface.

In the preparation of the present solutions using metallic magnesium with $CO_2$ and a combination of methanol and ethanol, it is therefore not necessary to rely on the use of surface-rich magnesium material, such as, for example, magnesium turnings or magnesium granules, as is required, for example, in the industrial production of magnesium ethoxide or magnesium methoxide. Instead, magnesium block material, which is cheaper and easier to handle in terms of safety, can be used.

Furthermore, no auxiliaries, such as, for example, mercury salts (cf. *Liebigs Annalen der Chemie*, 444, 236, 1925), are required for initiating the reaction. Thus, the achievable product purity when magnesium metal is used is slightly greater than that obtained when magnesium ethoxide and/or magnesium methoxide and/or their mixed alkoxide is used as the magnesium source.

Carbonation can be effected by passing gaseous $CO_2$ into, or by adding liquid or solid $CO_2$ to, a reaction mixture selected from the group consisting of:

(i) metallic magnesium and a combination of methanol and ethanol, (ii) magnesium ethoxide and methanol, (iii) magnesium ethoxide, magnesium methoxide and methanol, (iv) magnesium methoxide and ethanol, (v) magnesium methoxide, magnesium ethoxide and ethanol, (vi) a mixed alkoxide of the formula $Mg(CH_3O)_x (C_2H_5O)_y$, x and y each being greater than 0 and less than 2 and the sum of x and y being equal to 2, and either ethanol or methanol, and (vii) magnesium ethoxide and/or magnesium methoxide and/or their mixed alkoxide of the formula $Mg(CH_3O)_x (C_2H_5O)_y$, x and y each being greater than 0 and less than 2 and the sum of x and y being equal to 2, and a combination of methanol and ethanol.

Combinations of two or more of reaction mixtures (i)–(vii) above may also be employed, particularly a combination of one of reaction mixtures (i)–(v) and one of reaction mixtures (vi)–(vii). Thus, in the process of preparing the present storage-stable solution by reacting a magnesium alkoxide with $CO_2$, the reaction mixture may be a combination of a mixed alkoxide of the formula $Mg(CH_3O)_x (C_2H_5O)_y (CO_2)_n$, x and y each being greater than 0 and less than 2 and the sum of x and y being equal to 2, and one member of the group consisting of (i) magnesium ethoxide in methanol, (ii) magnesium ethoxide and magnesium methoxide in methanol, (iii) magnesium methoxide in ethanol and (iv) magnesium methoxide and magnesium ethoxide in ethanol.

The $CO_2$ content n of the present solution can be adjusted by metering gaseous, liquid or solid $CO_2$ into the mixture. In the context of the present application, "metering" refers to adding a measured amount of $CO_2$ into the reaction mixture.

In another variant, the $CO_2$ content n of the present solution can be adjusted by thermally expelling $CO_2$ from a solution of a mixture of carbonated magnesium methoxide, carbonated magnesium ethoxide and their carbonated mixed alkoxide in a combination of methanol and ethanol, the solution containing an excess of $CO_2$. Preferably, "thermally expelling" refers to heating a solution of a mixture of carbonated magnesium methoxide, carbonated magnesium ethoxide and their carbonated mixed alkoxide containing an excess of $CO_2$ at a temperature, under a reduced pressure and for a length of time sufficient to provide a $CO_2$ content n of from 1.0 to 2.2, preferably from 1.2 to 2.2.

Thermal expulsion may be conveniently conducted using a rotary evaporator. Suitable temperatures may include a bath or "bottom" temperature of from 10° C. to 80° C., more preferably from 20° C. to 50° C. Suitable pressures may include a reduced pressure of from 500 mbar to 5 mbar absolute, more preferably from 250 mbar to 10 mbar absolute.

The amount of $CO_2$ introduced can be easily monitored via the mass balance, by measuring the weight increase of the solution or reaction mixture after adding $CO_2$. The magnesium content of the present solution can also be adjusted by distilling excess methanol and/or ethanol from a solution of a mixture of carbonated magnesium methoxide, carbonated magnesium ethoxide and their carbonated mixed alkoxide in a combination of methanol and ethanol, when the solution contains excess methanol and/or ethanol.

Owing to the sensitivity of the present solutions to hydrolysis and to oxidation, all operations must be carried out in the absence of air and moisture.

The present invention also concerns a method for preserving paper, comprising applying a solution of a mixture of carbonated magnesium methoxide of the formula $Mg(CH_3O)_2 (CO_2)_n$, carbonated magesium ethoxide alkoxide of formula $Mg(C_2H_5O)_2 (CO_2)_n$ and a carbonated mixed alkoxide of the formula $Mg (CH_3O)_x (C_2H_5O)_y (CO_2)_n$ in a combination of methanol and ethanol, x and y each being greater than 0 and less than 2 and the sum of x and y being equal to 2, wherein the magnesium content of the solution is from 0.1 to 11% by weight, based on the total weight of the solution, and the $CO_2$ content n is from 1.0 to 2.2, to the paper. The solution can be applied to paper by any known method; for example, by dipping the paper into or passing the paper through the solution, or by spraying the solution onto the paper. The present solution may be diluted, preferably with a solvent selected from the group consisting of methanol, ethanol and a mixture thereof, prior to application to the paper.

The present invention also concerns a method for preparing a catalyst for the polymerization of olefins, comprising forming spherical magnesium methoxide, magnesium ethoxide or a mixture thereof from a solution of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, wherein the magnesium content of the solution is from 0.1 to 11% by weight, based on the total weight of the solution, and the $CO_2$ content n is from 1.0 to 2.2. The spherical magnesium methoxide and magnesium ethoxide can be prepared by conventional methods; for example, by spray drying the present carbonated magnesium alkoxide solution, or precipitating carbonated magnesium alkoxide from the present solution, to form a solid magnesium alkoxide mixture. If required, the solid magnesium alkoxide mixture may be subsequently decarbonated by methods known in the art, such as heating (for example, to a temperature of from 20° C. to 200° C.) under vacuum.

Other features of the invention will become apparent in the course of the following descriptions of exemplary embodiments which are given for illustration of the invention and are not intended to be limiting thereof.

EXAMPLE 1:

Preparation of a storage-stable solution of a mixture of carbonated magnesium methoxide, carbonated magnesium ethoxide and their carbonated mixed alkoxide by reacting magnesium ethoxide in methanol with $CO_2$ 470 g of methanol are placed in a three-necked flask equipped with a reflux condenser, a gas inlet tube, a nitrogen blanketing system and a KPG blade stirrer, and 200 g of magnesium ethoxide (manufacturer: Hüls AG) are then added thereto while blanketing the reaction system with nitrogen. Gaseous $CO_2$ is passed in while stirring. The $CO_2$ absorption is monitored continuously by checking the weight of the reaction solution. The temperature in the reaction vessel increases continuously. The reaction is terminated after absorption of 92 g of $CO_2$, corresponding to a $CO_2$ content n of 1.12. The virtually colorless solution has a color number of <1 (measured according to "Gardner"), and has a magnesium content of 6% by weight. The characteristics of the solution are unchanged after a storage for 6 weeks in a tightly sealed glass bottle. No discoloration, precipitation or gelling occurs.

EXAMPLE 2:

Preparation of a storage-stable solution of a mixture of carbonated magnesium methoxide, carbonated magnesium ethoxide and carbonated mixed alkoxide having a high magnesium concentration 470 g of methanol are placed in a three-necked flask equipped with a reflux condenser, a gas inlet tube, a nitrogen blanketing system and a KPG blade stirrer, and 200 g of magnesium ethoxide (manufacturer: Hüls AG) are then added while blanketing the reaction system with nitrogen. Gaseous $CO_2$ is passed in while stirring. The $CO_2$ absorption is monitored continuously by checking the weight of the reaction solution. The temperature in the reaction vessel increases continuously. The reaction is terminated after absorption of 135 g of $CO_2$, corresponding to a $CO_2$ content n of 1.75. The virtually colorless solution has a magnesium content of 5.7% by weight.

In order to establish a higher magnesium concentration, 500 g of the solution are evaporated down over a period of about 3 hours in a rotary evaporator, at a bottom temperature increasing from 20° to 40° C. and at a pressure decreasing from 220 to 10 mbar absolute. During this procedure, the solution loses about 26 g of $CO_2$ and 215 g of solvent (mixture of methanol and ethanol). The $CO_2$ content n of the viscous solution is 1.2, the magnesium content is 11% by weight and the color number is <1 (measured according to "Gardner"). The solution is unchanged after storage for 6 weeks in a tightly sealed glass bottle. No coloration, precipitation or gelling occurs.

Obviously, numerous modifications and variations of the present invention are possible in light of the above teachings. It is therefore to he understood that, within the scope of the appended claims, the invention may be practiced otherwise than as specifically described herein.

What is claimed as new and desired to be secured by Letters Patent of the United States is:

1. A storage-stable solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, wherein the magnesium content of the solution is from 0.1 to 11% by weight, based on the total weight of the solution, and the $CO_2$ content n is from 1.0 to 2.2.

2. The solution of claim 1, wherein the magnesium content of the solution is from 3 to 11% by weight.

3. The solution of claim 1, wherein the magnesium content of the solution is from 5.7 to 6% by weight, the $CO_2$ content n is from 1.12 to 1.75 and no coloration, precipitation or gel formation occurs in said solution after storage for six weeks in a sealed glass bottle.

4. A method for preserving paper, comprising applying a solution of a mixture of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, wherein the magnesium content of the solution is from 0.1 to 11% by weight, based on the total weight of the solution, and the $CO_2$ content n is from 1.0 to 2.2, to said paper.

5. A method for preparing a catalyst for the polymerization of olefins, comprising forming spherical magnesium methoxide, magnesium ethoxide or a mixture thereof from a solution of carbonated magnesium methoxide of the formula $Mg(CH_3O)_2 (CO_2)_n$, carbonated magnesium ethoxide of the formula $Mg(C_2H_5O)_2 (CO_2)_n$ and a carbonated mixed alkoxide of the formula $Mg(CH_3O)_x (C_2H_5O)_y (CO_2)_n$ in a combination of methanol and ethanol, x and y each being greater than 0 and less than 2 and the sum of x and y being equal to 2, wherein the magnesium content of the solution is from 0.1 to 11% by weight, based on the total weight of the solution, and the $CO_2$ content n is from 1.0 to 2.2.

* * * * *